US 6,660,506 B2

(12) United States Patent
Nguyen et al.

(10) Patent No.: US 6,660,506 B2
(45) Date of Patent: Dec. 9, 2003

(54) ETHANOL PRODUCTION WITH DILUTE ACID HYDROLYSIS USING PARTIALLY DRIED LIGNOCELLULOSICS

(75) Inventors: Quang A. Nguyen, Chesterfield, MO (US); Fred A. Keller, Lakewood, CO (US); Melvin P. Tucker, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 10/344,091

(22) PCT Filed: Apr. 26, 2001

(86) PCT No.: PCT/US01/13365
§ 371 (c)(1),
(2), (4) Date: Feb. 7, 2003

(87) PCT Pub. No.: WO02/18610
PCT Pub. Date: Mar. 7, 2002

(65) Prior Publication Data
US 2003/0199049 A1 Oct. 23, 2003

Related U.S. Application Data

(63) Continuation-in-part of application No. 09/634,978, filed on Aug. 9, 2000, now Pat. No. 6,423,145.

(51) Int. Cl.$^7$ ............................. C12P 7/10; C13K 1/02
(52) U.S. Cl. ............................................ 435/165; 127/37
(58) Field of Search ............................. 127/37; 435/165

(56) References Cited

U.S. PATENT DOCUMENTS

| 3,939,286 | A | * | 2/1976 | Jelks | 426/312 |
| 4,461,648 | A | * | 7/1984 | Foody | 127/37 |
| 5,536,325 | A | * | 7/1996 | Brink | 127/43 |
| 6,423,145 | B1 | * | 7/2002 | Nguyen et al. | 127/37 |

FOREIGN PATENT DOCUMENTS

| EP | 0 091 221 A2 | 10/1983 |
| EP | 0 187 422 A2 | 7/1986 |

* cited by examiner

Primary Examiner—David Brunsman
(74) Attorney, Agent, or Firm—Paul J. White

(57) ABSTRACT

A process of converting lignocellulosic biomass to ethanol, comprising hydrolyzing lignocellulosic materials by subjecting dried lignocellulosic material in a reactor to a catalyst comprised of a dilute solution of a strong acid and a metal salt to lower the activation energy (i.e., the temperature) of cellulose hydrolysis and ultimately obtain higher sugar yields.

23 Claims, 3 Drawing Sheets

ETHANOL PRODUCTION WITH DILUTE ACID HYDROLYSIS USING PARTIALLY DRIED LIGNOCELLULOSICS

This is a continuation-in-part of U.S. patent application Ser. No. 09/634,978 filed Aug. 9, 2000, now U.S. Pat. No. 6,423,145.

CONTRACTUAL ORIGIN OF THE INVENTION

The United States Government has rights to this invention pursuant to Contract No. DE-AC36-99GO-10337 between the United States Department of Energy and the Midwest Research Institute.

TECHNICAL FIELD

The invention relates to hydrolyzing lignocellulosic materials by subjecting dried lignocellulosic material in a reactor to a catalyst comprised of a dilute solution of a strong acid and a metal salt to lower the activation energy (i.e., temperature) of cellulose hydrolysis and ultimately obtain higher sugar yields. The lower temperature obtained occasions a reduction in the cost of steam and equipment and enables the hydrolysis of both hemicellulose and cellulose, when used with hydrolyzer feeders that do not compact the biomass feedstock to achieve higher sugar yields.

Lignocellulose is ubiquitous in all wood species and all agricultural and forestry waste. In addition, municipal waste, which typically contains about half waste paper and yard waste, is a source of lignocellulosic materials. Currently, municipal waste is buried or burned at considerable expense to the disposer or the government organization providing solid waste services.

Lignocellulosic biomass is a complex structure of cellulose fibers wrapped in a lignin and hemicellulose sheath. The ratio of the three components varies depending on the type of biomass. Typical ratios are as follows:

|  | Softwoods | Corn Cobs | RDF* |
| --- | --- | --- | --- |
| Cellulose | 42% | 40% | 52% |
| Hemicellulose | 25% | 36% | 26% |
| Lignin | 28% | 13% | 20% |

*RDF = Refuse Derived Fuel from municipal systems waste

Different woods also have different compositions. Softwoods (gymnosperms) generally have more glucomannan and less glucuronoxylan than hardwoods and grasses (angiosperms).

Cellulose is a polymer of D-glucose with β [1Ō4] linkages between each of the about 500 to 10,000 glucose units. Hemicellulose is a polymer of sugars, primarily D-xylose with other pentoses and some hexoses with β [1Ō4] linkages. Lignin is a complex random polyphenolic polymer. Therefore, lignocellulose represents a very cheap and readily available substrate for the preparation of sugars, which may be used alone or microbially fermented to produce alcohols and other industrial chemicals.

Ethanol, one of the alcohols, which can be produced from lignocellulosic biomass, has a number of industrial and fuel uses. Of particular interest is the use of ethanol as an additive to gasoline to boost octane, reduce pollution and to partially replace gasoline in the mixture. This composition is the well-known commercial product called "gasohol." It has been proposed to eliminate gasoline completely from the fuel and to burn ethanol alone. Such a fuel would produce considerably less air pollution by not forming as much carbon monoxide or hydrocarbon emissions. Furthermore, gasoline is produced from crude oil; which fluctuates in price, availability, and is the subject of unpredictable world politics.

It has been estimated that about $1 \times 10^9$ tons of lignocellulosic wastes are produced every year. This amount exceeds the total amount of crude oil consumed per year. In theory, if properly managed, the lignocellulose produced by the United States is sufficient to produce all of the country's needs for liquid fuel if the cellulose and hemicellulose can be completely converted into ethanol. The amount of energy theoretically obtainable from the combustion of cellulose or the glucose or alcohol derived therefrom is about 7200 BTU per pound or roughly equivalent to 0.35 pounds of gasoline. Hemicellulose has similar value when converted into sugars or ethanol. Consequently, cellulose and hemicellulose represent a readily available potential source for ethanol production. The technology for the production of ethanol from grain and fruit for beverage purposes has been well developed for centuries. However, the costs have been relatively high compared to the cost of gasoline. Accordingly, many methods have been proposed to reduce the cost and increase the efficiency of ethanol production.

Among the techniques proposed for the production of fuel grade ethanol include the hydrolysis of cellulose and hemicellulose to produce sugars which can be fermented to produce ethanol. Cellulose in the form of wood, newsprint and other paper, forest, agricultural, industrial and municipal wastes is quite inexpensive compared to grain, fruit, potatoes or sugarcane which is traditionally used to prepare alcohol beverages.

Hydrolysis of lignocellulosic biomass using an acid catalyst to produce sugars has been known for decades but can be costly and requires special equipment. The hydrolyzed sugars themselves are somewhat labile to the harsh hydrolysis conditions and may be degraded to unwanted or toxic byproducts. If exposed to acid for too long, the glucose derived from cellulose degrades into hydroxymethlylfurfural, which can be further degraded into levulinic acid and formic acid. Xylose, a hemicellulose sugar, can be degraded into furfural and further to tars and other degradation products.

In order for acid to completely hydrolyze the cellulose and hemicellulose in a lignocellulosic substrate, degradation of the desirable sugars and formation of the toxic byproducts cannot be avoided due to kinetic constraints. On the other hand, to use conditions sufficiently gentle that significant degradation of sugars will not occur does not result in complete hydrolysis of substrate. Furthermore, the acid is corrosive and requires special handling and equipment. Accordingly, in the last twenty years attention has focused on enzymatic hydrolysis of cellulose with cellulase followed by fermentation of the resulting sugars to produce ethanol which in turn is distilled to purify it sufficiently for fuel uses.

Cellulase is an enzyme complex that includes three different types of enzymes involved in the saccharification of cellulose. The cellulase enzyme complex produced by Trichoderrna reesei QM 9414 contains the enzymes named endoglucanase (E.C. 3.2.1.4), cellobiohydrolase. (E.C.3.2.1.91) and β-glucosidase (E.C.3.2.1.21). Gum et al. *Biochem. Biophys.Acta*, 446:370–86 (1976). The combined synergistic actions of these three enzymes in the cellulase preparation completely hydrolyses cellulose to D-glucose.

However, cellulase cannot completely degrade the cellulose found in native, unpretreated lignocellulose. It appears that the hemicellulose and lignin interfere with the access of the enzyme complex to the cellulose, probably due to their coating of the cellulose fibers. Furthermore, lignin itself can bind cellulase thereby rendering it inactive or less effective for digesting cellulose. For example, raw ground hardwood is only about 10 to 20% digestible into sugars using a cellulase preparation.

BACKGROUND ART

U.S. Pat. No. 4,529,699 discloses a process for obtaining ethanol by continuous acid hydrolysis of cellulosic materials by providing a homogenized slurry of heated (160° to 250° C.) cellulosic material continuously into a reactor, adding concentrated acid to the pressurized and heated cellulosic material to obtain hydrolysis, neutralizing and fermenting the resulting aqueous solution to obtain ethanol, and recovering resulting byproducts of methanol, furfural, acetic acid and lignin.

A process for the production of sugars and optionally cellulose and lignin from lignocellulosic raw materials is disclosed in U.S. Pat. No. 4,520,105. The process entails subjecting vegetable materials to a chemical pretreatment with a mixture of water and lower aliphatic alcohols and/or ketones at 100° C. to 190° C. for a period of from 4 hours to 2 minutes with control of the breakdown of the hemicellulose components followed by separation of residue and a subsequent chemical treatment with a similar solvent mixture at elevated temperatures for a period of from 6 hours to 2 minutes.

U.S. Pat. No. 5,411,594 discloses a hydrolysis process system for continuous hydrolysis saccharification of lignocellulosics in a two-stage plug-flow-reactor system. The process utilizes dilute-acid hydrolysis and is primarily by reverse inter-stage transfer-flow, opposite to biomass, of second-stage surplus of: process heat; dilute-acid; and ingredient and solution water, all in an alpha cellulose hydrolysate, dilute-acid solution. The primary final product is the combined hydrolysate sugars in a single solution, including pentose, hexose and glucose sugars, which are fermented into ethanol and/or Torula yeast. The secondary final solid product is an unhydrolyzed lignin solid.

A method of treating biomass material using a two-stage hydrolysis of lignocellulosic material is disclosed in U.S. Pat. No. 5,536,325. The conditions during the first stage is such as to hydrolyze or depolymerize the hemicellulosic component without substantial degradation of resulting monosaccharides and conditions during the second stage being such as to hydrolyze the cellulose to glucose without substantial degradation of the glucose. Hydrolysis in both stages is accomplished by the use of nitric acid, and the pH, retention time, and temperature in both stages are selected to maximize production of the desired monosaccharide or monosaccharides.

U.S. Pat. No. 6,022,419 discloses a multi-function process for hydrolysis and fractionation of lignocellulosic biomass to separate hemicellulosic sugars from other biomass components such as extractives and proteins; a portion of the solubilized lignin; cellulose; glucose derived from cellulose; and insoluble lignin form the biomass by introducing a dilute acid into a continual shrinking bed reactor containing a lignocellulosic material at 94° to 160° C. for 10 to 120 minutes at a volumetric flow rate of 1 to 5 reactor volumes to solubilize extractives, lignin, and protein by keeping the solid-to-liquid ratio constant throughout the solubilization process.

A process for rapid acid hydrolysis of lignocellulosic material is disclosed in U.S. Pat. No. 5,879,463. The process is a continuous process for acid hydrolysis of lignocellulosic material through which delignification and saccharification are carried out in a single reaction cycle employing a solubilizing organic solvent of lignin and a strong and extremely diluted inorganic acid to obtain highly concentrated recoveries of sugar.

There is a need in the art of using lignocellulosic materials to obtain fermentable sugars for production of ethanol, to develop more effective pretreatment methods that result in high hemicellulose sugar yield and high enzymatic cellulose digestibility, all of which result in greater yields of ethanol.

Disclosure of Invention

One object of the present invention is to provide more effective lignocellulosic pretreatment methods that entail drying acid-impregnated lignocellulosic biomass, that result in higher hemicellulose sugar yields and higher enzymatic cellulose digestibility en route to producing ethanol.

Another object of the present invention is to provide pre-hydrolysis conditions for lignocellulosic materials by subjecting an acid-soaked feedstock to drying (using heated gas such as air, nitrogen or carbon dioxide, or superheated steam, or any combination of heated gas and steam), which is believed to reduce compaction and thereby lessen collapse of cells in pressed chips to permit good mass and heat transfer to achieve even cooking and higher overall sugar for production of ethanol.

A further object of the present invention is to provide post hydrolysis fermentation conditions for dried lignocellulosic materials using a two-stage fermentation process, wherein the first fermentation operates under microaerobic conditions to maintain adequate yeast cell concentration that is forwarded to a second-stage fermenter during the growth phase to enable the yeast to achieve 90% ethanol yield from fermentable sugars without the need for detoxification of the hydrolysate liquor.

In general, the invention process for converting lignocellulosic biomass to ethanol employs: a two-stage dilute acid hydrolysis process that hydrolyzes partially dried, acid-impregnated lignocellulosic biomass to fermentable sugars; a countercurrent extraction process to recover over 95% of soluble sugars from the first-stage hydrolysate with minimal dilution of sugar solution; and a two-stage fermentation process which incorporates yeast recycle in the first-stage liquid fermentors (the first fermentor operates under microaerobic conditions to maintain adequate yeast cell concentration, wherein a first-stage fermentation broth is forwarded to second-stage fermentors during the growth phase of the yeast, and the second-stage fermentation is carried out in slurry fermentors).

The process enables the yeast to achieve 90% ethanol yield from fermentable sugars without the need for detoxification of the hydrolysate liquor. This adaptation method also reduces nutrient requirements. Furthermore, the second-stage slurry fermentation eliminates the need for washing the second-stage hydrolysate to recover soluble sugars.

BEST MODE FOR CARRYING OUT THE INVENTION

Figure 1:
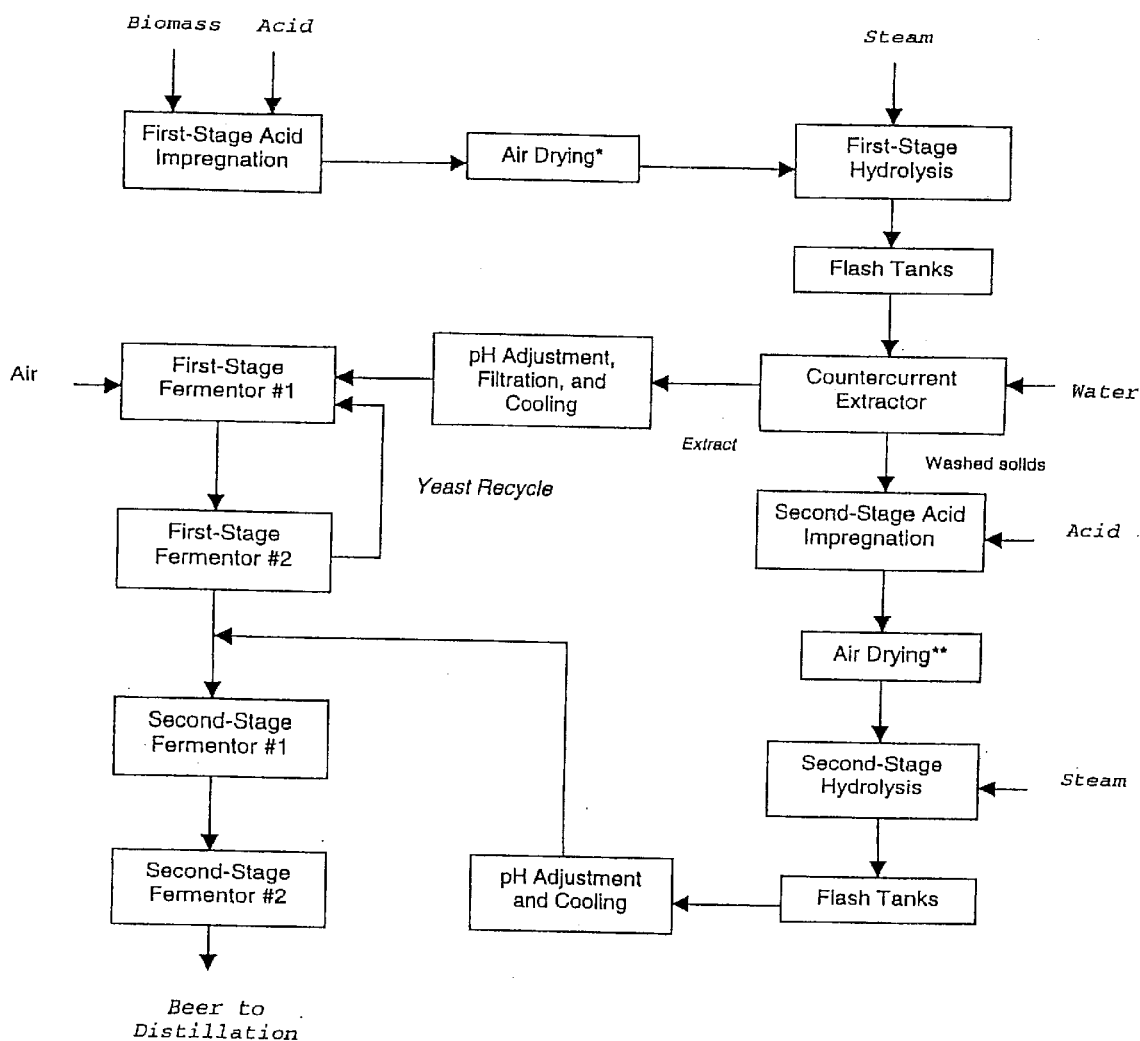
FIG. 1 is a process block flow diagram showing production of ethanol from the invention process using partially dried lignocellulosic biomass.

Some major hurdles in the development of commercially feasible biomass-to-ethanol processes are: (i) the high cost of cellulase enzymes; and (ii) the need to develop effective pretreatment methods that result in high hemicellulose sugar yield and high enzymatic cellulose digestibility.

Currently, two-stage dilute acid hydrolysis appears to be the leading technology; however, while this technology has been demonstrated at pilot and commercial scale, improvements in sugar and ethanol conversion yields are necessary to make the process commercially viable even where low-cost feedstock is available. In this connection, most two-stage dilute acid hydrolysis processes developed to date require a detoxification step (usually by overliming) to improve the fermentability of the hydrolysates and ethanol yield. The overliming method produces a large quantity of gypsum; which poses a disposal problem.

We have developed a method for adapting yeast to the inhibitors in softwood hydrolysates so that high ethanol yield (90%) can be obtained without overliming requirements. The method employs two mutant *Saccharomisyces cerevisiae* yeasts.

We have also adapted a xylose fermenting yeast strain *Pichia stipitis* to softwood hydrolysates. The yeast adaptation method is incorporated in the overall process design by including a yeast recycle loop in the first-stage fermentation.

Another challenge in the development of commercially feasible biomass-to-ethanol processes is scaling up the hydrolysis reactors. At present, most commercial scale reactors are batch percolators. Although several continuous pilot hydrolyzers are in operation (e.g., Tennessee Valley Authority, Muscle Shoals, Ala., and the National Renewable Energy Laboratory, Golden, Colo.), these continuous reactors are yet to be proven, especially at high pressure and high temperature conditions used in the second stage.

Research on two-stage dilute acid hydrolysis processes for converting softwood forest thinnings has been performed in a 4-L batch steamer digester (also called a steam gun). Hemicellulose sugar yields of 85%–90% and glucose yields of 55%–60% were achieved. Process simulation and cost evaluation indicate that the amount of water used in the process (such as water added in the acid impregnation step and wash water used to recover hemicellulose sugars from first-stage hydrolysate) has a significant impact on the production cost. Although some process water can be recycled, large volumes of water in the system would result in larger equipment size and lower product concentrations. Therefore, it is critically important to minimize the amount of water added to the hydrolyzers (i.e., water entrained in biomass feed) and the hemicellulose sugar extraction system (i.e., wash water).

Because of the low cost and relative ease of handling, sulfuric acid is used in the two-stage dilute acid hydrolysis process. Acid impregnation is achieved by soaking the biomass in dilute acid solution, under elevated temperature and pressure. Excess acid solution is then removed from the biomass, normally by pressing via a screw press. Most continuous biomass hydrolyzers (such as the Sunds Hydrolyzer, the Pandia Reactor, and the Stake II Reactor) employ screw feeders to feed biomass into the reactor under pressure. These compression feeders create a dense biomass plug to seal the reactor. The pressure in the screw feeders (i.e., certain Sunds screw feeders) can reach as high as 1,200 psig. At this pressure the solid content of sawdust particles is increased to about 70%.

Figure 2:
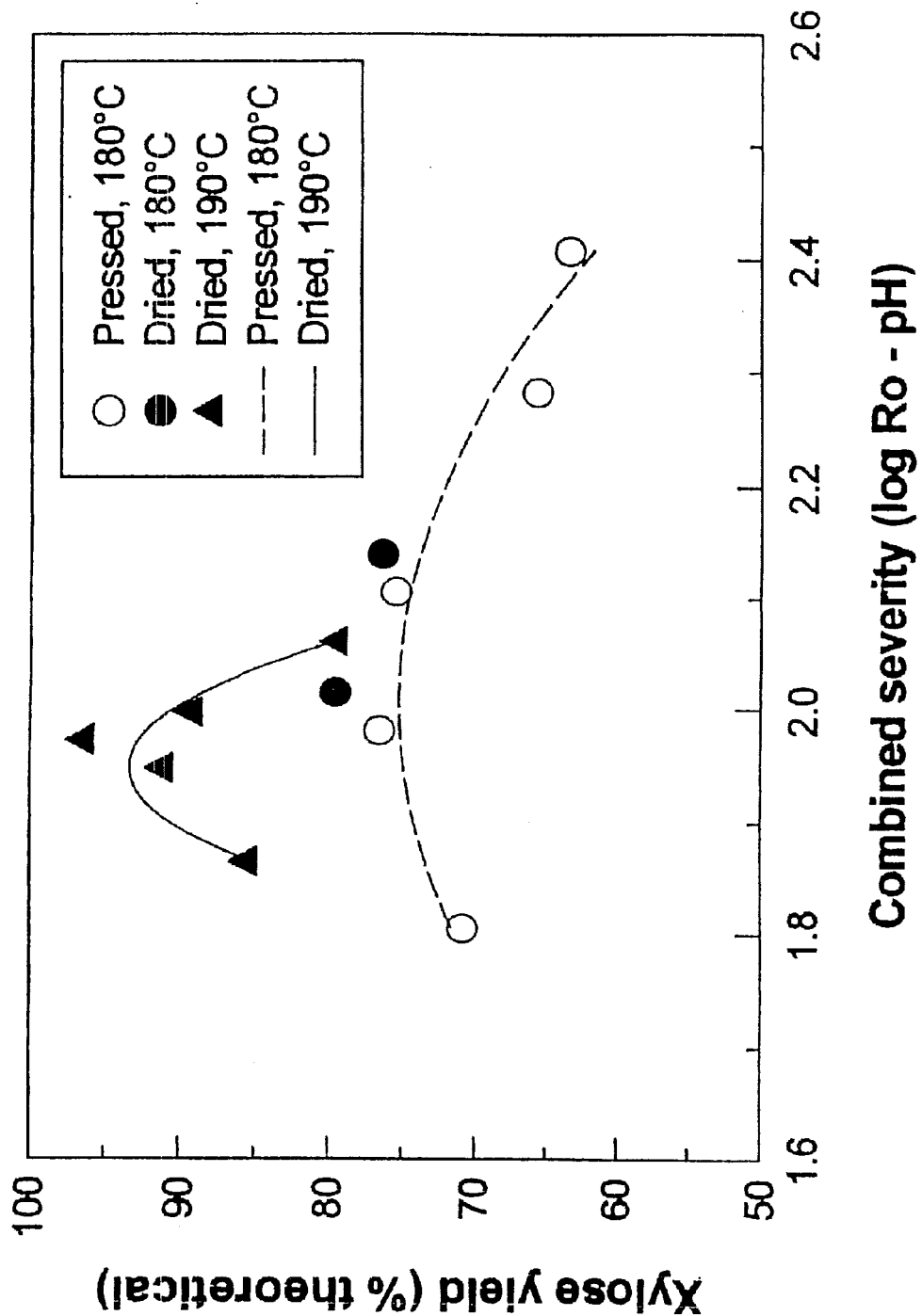
FIG. 2 is a graph depicting xylose yield from first-stage dilute acid hydrolysis of corn stover when hydrolyzed with dilute sulfuric acid at 180° C. to 190° C.

Experimental results clearly show that pressing acid-soaked biomass from a starting solid content of 33% to 45% before hydrolysis using the batch digester lowers the soluble hemicellulosic sugar yield approximately 10% in comparison with biomass that are air-dried to the same solids content. This is clearly shown in FIG. 2 where air drying in comparison with pressing acid-soaked corn stover to the same solid and acid contents generally produces higher xylose yields in dilute acid hydrolysis. The Combined Severity Factor (Log Ro-pH)[1] is used to describe the severity of dilute acid catalyzed steam pretreatment. The reaction ordinate $Ro^2$ is given by the following expression:

$$Ro = t * \exp[(T-100)/14.75]$$

where t is the reaction time in minutes;

T is the reaction temperature in degree Celsius;

* is multiplication; and exp is the exponential

The acid concentrations in both types of chips are essentially the same in this comparison test.

Figure 3:
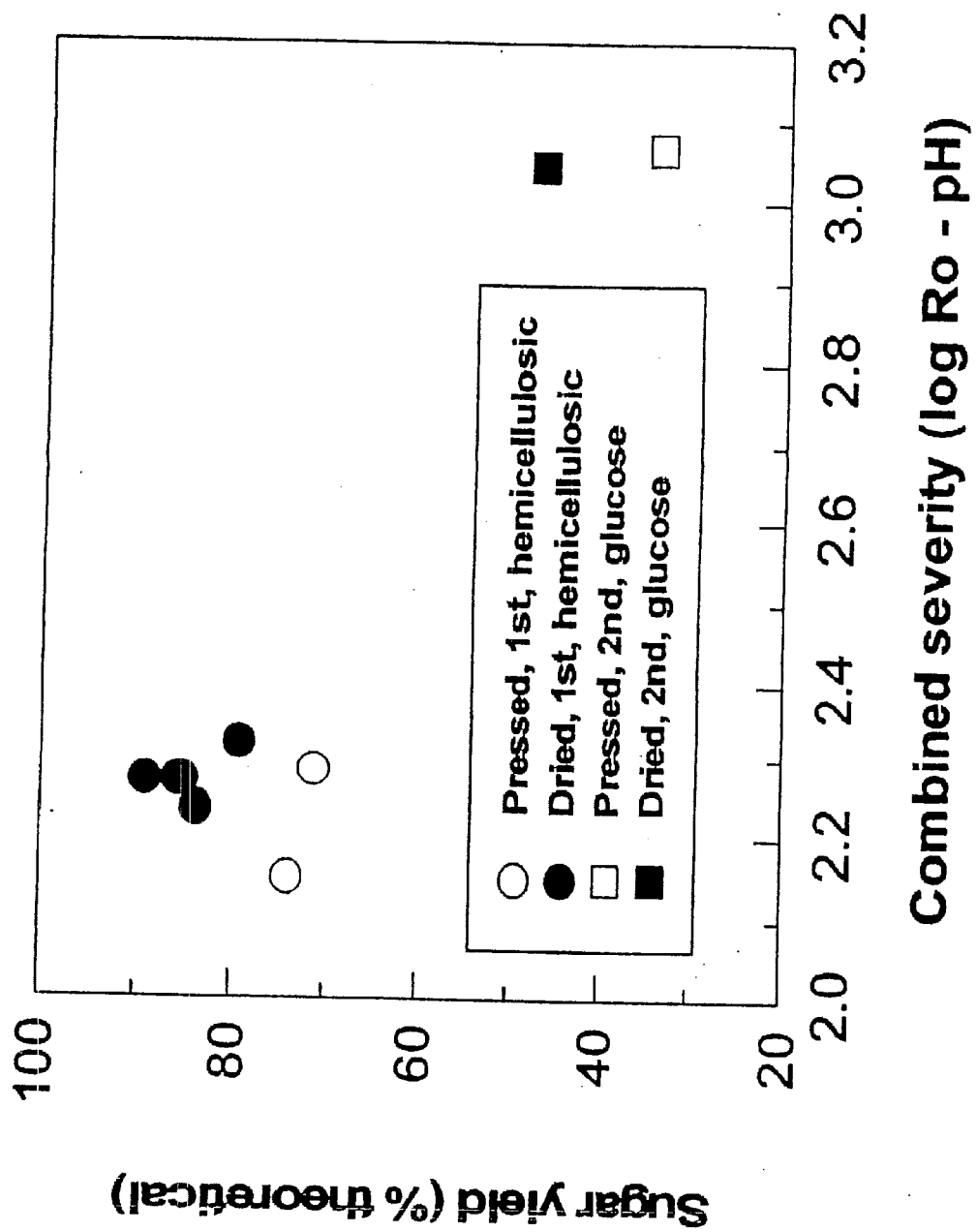
FIG. 3 is a graph depicting hemicellulose sugar yield from first-stage and glucose yield from second-stage from a dilute solution of a strong acid hydrolysis of whole-tree softwood forest thinnings.

The difference in sugar yield is even more dramatic for wood chips as shown in FIG. 3, which depicts hemicellulose sugar yield from first stage and glucose yield from second stage dilute acid hydrolysis of whole-tree softwood forest thinnings. One possible explanation for the lower sugar yield for pressed chips is that some cells in the pressed chip collapse. As a result, good mass and heat transfer are not achieved in compacted chips, which leads to uneven cooking of the batch and lower overall sugar yield. The implication of this observation is important regarding the selection of hydrolyzer and feeder design.

Continuous compression feeders, which compact biomass particles and collapse cell walls tend to lead to uneven heating of biomass particles and lower sugar yield. To ensure the integrity of the acid-impregnated biomass particles, certain features have been included in the process design. These include an acid impregnator which does not squeeze the biomass to higher than about 35% solids content, an air-drier (or a centrifuge) to increase the solids content of acid-soaked biomass to about 45% solids, and a hydrolyzer design which does not use compression screw feeders. Batch or continuous steam digesters using non-pressurized gravity feeders or pressurized gravity feeders (such as pressurized lock-hoppers) or rotary valve feeders are most suitable for application in both first-and second-stage hydrolysis.

A countercurrent extractor is used to recover soluble sugars from first-stage hydrolysate with minimal use of wash water. To preserve the integrity of insoluble solids, the extractor is controlled so as not to squeeze the solid particles to higher than about 35% solids. A countercurrent screw-conveyor extractor or a vacuum belt washer is suitable for recovering soluble sugars from first-stage hydrolysate. The screw extractor is more efficient in water usage, and in recognition that it is very difficult and costly to wash soluble sugars from the mud-like second-stage hydrolysate, no second-stage washers have been employed. Instead, the second-stage hydrolysate is slurried with the first-stage fermentation broth and sent to the second stage fermentors.

EXAMPLES

First-stage Acid Impregnation

Moist biomass feedstock of between 35% and 50% by weight solids content is fed into an acid impregnator. The feedstock may consist of wood chips, sawdust, milled agricultural residues, or corn-refining residue. The design of the acid impregnator is dependent upon the type of acid used. If gaseous sulfur dioxide is used, no water is added. If another strong acid such as sulfuric, hydrochloric, or nitric or any strong acid which effect pH values below about 3, is used, a dilute solution of one of these acids is heated from about 40° C. to about 80° C. before adding to the impregnator. Optionally, a small amount of a metal salt catalyst (such as ferrous sulfate) is added in an amount sufficient to provide higher overall fermentable sugar yields than is obtainable when hydrolyzing with dilute acid alone. In order to thoroughly soak the biomass in the acid solution, a residence time of about 1 to 3 hours is required. For gaseous sulfur dioxide, the contact time is shorter or in the vicinity of less than 30 minutes. The acid-soaked feedstock is drained or squeezed to about 35% solids upon exiting the impregnator. The feedstock is further dewatered to about 40% to about 60% solids using either a dryer or a centrifuge (if gaseous $SO_2$ is used and if the solid content of biomass feedstock is between about 40% and about 60% by weight, dewatering is not necessary). A dryer (using heated air or gas such as nitrogen or carbon dioxide, superheated steam or any combination of steam and heated air or gas) is superior because the centrifuge tends to cause compaction of biomass particles. If sulfuric acid is used, the acid concentration of the liquid in the biomass prior to feeding into the first-stage hydrolyzers is in the range of from about 0.3% to about 4.0% by weight.

First-stage Hydrolysis

The acid-impregnated biomass is fed into the first-stage hydrolyzer via a non-pressurized or pressurized gravity feeder or rotary valve feeder that does not compact or densify the biomass particles. The hydrolyzer may be a batch or continuous hydrolyzer. Steam is directly injected into the hydrolyzer in order to heat the biomass to the desired temperature. The hydrolysis is conducted at a temperature of from about 130° C. to about 220° C. for a period of from about 1 to about 60 minutes. Thereafter, the hydrolysate is discharged into a flash tank operating at a temperature of from about 120° C. to about 140° C., and is held there for a period of from about 1 to about 3 hours to hydrolyze most of the soluble oligosaccharides to monomeric sugars. The hydrolysate from the first flash tank is then flashed into a second flash tank operating at a temperature of about 95 ° C. The second flash tank serves as a feed surge tank for the countercurrent extractor.

Counter-current Extractor

In excess of 95% of soluble sugars from the first-stage hydrolysate slurry is recovered by the counter-current extractor (which may be a screw-conveyor extractor or a vacuum belt extractor). The hydrolysate is washed with hot water at a temperature of from about 50° C. to about 80° C., wherein the water is used in a ratio of from about 4/1 for liquid-to-insoluble solids. Alkali (lime or ammonia) is added to the extract to bring the pH to about 5. If lime is used, the precipitates (mostly gypsum) are filtered out of the extract and the filtrate is forwarded to the first stage fermentors. The extracted solids are dewatered to about 35% solids, and conveyed to the second-stage acid impregnator.

Second-stage Acid Impregnation

The second-stage acid impregnator may be similar in design to the first-stage impregnator. The insoluble solids from the extractor are soaked in an aqueous solution of a dilute acid catalyst and a metal salt catalyst sufficient to provide higher overall fermentable sugar yields than is obtainable when hydrolyzing with dilute acid alone. A strong acid such as sulfuric, hydrochloric, nitric, $SO_2$ or any strong acid, which effect pH values below about 3 and a metal salt catalyst selected from the group consisting of ferrous sulfate, ferric sulfate, ferric chloride, aluminum sulfate, aluminum chloride, and magnesium sulfate, may be used.

The acid-soaked biomass (washed first-stage solids) is dewatered using a dryer or a centrifuge to about 45% solids. If gaseous $SO_2$ is used, the washed solids are impregnated with an aqueous solution of a metal salt catalyst, then dried to about 45% solids before entering the SO2 impregnator. The dryer is preferred due to the risk of compaction of biomass particles when using the centrifuge. The acid concentration of liquid in the acid-impregnated biomass prior to feeding into the second-stage hydrolyzers is in the range of from about 0.5 to 4% by weight, and the concentration of the metal salt catalyst is between about 0.2 mmole/L and about 25 mmole/L.

Second-stage Hydrolysis

Acid and metal salt-impregnated biomass is fed into the second-stage hydrolyzer using gravity feeders or rotary valve feeders that do not densify the biomass particles. The hydrolyzer may be batch or continuous. To heat the biomass to the desired temperature, steam is injected directly into the hydrolyzer to create hydrolysis temperatures of from about 190° C. to about 240° C. for a period of from about 1 to about 10 minutes. The hydrolysate is then discharged into a flash tank operating at a temperature of from about 120° C. to about 140° C. for a period of from about 1 to about 3 hours to hydrolyze most of the soluble oligosaccharides to monomeric sugars. The hydrolysate from the first tank is then flashed into a second flash tank operating at a temperature of about 95° C. The second flash tank serves as a feed surge tank for the second-stage fermentors.

Ethanol Fermentation

Ethanol fermentation is carried out in two stages to incorporate the yeast adaptation and recycle feature.

First-stage Fermentation:

The pH-adjusted and filtered extract from the countercurrent extractor is cooled to about 32° C. to about 42° C. depending upon yeast strain and adaptation, and fed to the bottom of the first fermentor of a two-fermentor train connected in series. Each fermentor has a residence time of about 8 hours. Air is sparged into the bottom of the first fermentor (through air distributors) at a rate equivalent to about 0.05 volume of air per fermentor volume per minute (vvm). Air addition promotes some yeast growth to make up for the loss through the second-stage fermentors. The first fermentor is equipped with a side-entry mixer to keep the yeast cells in suspension, although side entry is not a necessary requirement of this invention. Corn steep liquor and ammonium sulfate may be added as nutrients to the feed stream to promote yeast growth. The broth from the first fermentor overflows into the top of the second fermentor. Inclined plates and a yeast sump are installed in the bottom of the second fermentor to facilitate yeast separation. Most of the yeast settling in the yeast sump is pumped back in with the feed into the first fermentors. Broth from the second fermentor (still containing some yeast) is forwarded to the first of the second-stage fermentors. The residence time of the first-stage fermentation is varied by controlling the liquid level in the second fermentor. The residence time is controlled such that yeast leaving the second fermentor in the first-stage fermentation train is in the growth phase. When softwood hydrolysate is used, the first-stage fermentation residence time is approximately 16 hours. Yeast is the preferred fermenting organism. The first fermentor may be seeded with one or a mixed culture of hexose-fermenting yeast and xylose-fermenting yeast.

Second-stage Fermentation

Alkali such as lime or ammonia is added to the second-stage hydrolysate slurry to adjust the pH to about 4.5. The slurry is cooled, using a slurry cooler, to about 32° C. to 42° C. depending upon yeast strain and adaptation method, and then mixed with the first-stage fermentation broth. Thereafter, the slurry is fed into the top of the first fermentor of a two-fermentor train. Broth exiting the first fermentor in the second-stage fermentation train at the bottom is pumped to the top of the second fermentor. Both fermentors are equipped with side-entry mixers to keep the insoluble solids in suspension. Side entry mixers are not essential to this invention. The residence time in each fermentor is about 8 hours. At the end of the second-stage fermentation, more than 95% of the fermentable sugars have been consumed. The fermentation broth is then pumped into a beer well, which serves as a surge tank for both fermentation and distillation systems.

Distillation

Ethanol is recovered from the beer by conventional distillation methods. The trays of the beer column are designed to handle the insoluble solids.

Insoluble Solids Recovery

The beer column bottom stream is centrifuged to recover most of the suspended solids. The centrifuge cake is further dewatered to approximately 50% total solids using a press (filter press, belt press or screw press) before being sent to the biomass boiler.

FIG. 1 is a block flow diagram of the production of ethanol from lignocellulosic biomass using the two-stage dilute acid process, as modified by the present invention.

In the process of FIG. 1, the drying step as shown by the block with the single asterisk is not necessary if gaseous $SO_2$ is used in the first-stage acid impregnation step. However, if the gaseous acid $SO_2$ is used, the washed pretreated biomass material is impregnated with a solution of a metal salt catalyst, then dried as shown by the block with the double asterisks to about 45% solids before entering the second-stage acid impregnator (i.e., the drying step precedes the acid-impregnation step).

The single asterisk in FIG. 1 is to signify that drying is not necessary if gaseous $SO_2$ is used in the first-stage acid impregnation.

The double asterisk in FIG. 1 indicates that, if gaseous $SO_2$ is used, the washed biomass material is dried to about 40%–60% solids before entering the acid impregnator (i.e., the drying steps precedes the acid-impregnation step).

What is claimed is:

1. In a process for converting lignocellulosic biomass to ethanol, the improvement of obtaining higher fermentable soluble sugar yields by drying acid impregnated biomass particles, comprising:

a) feeding a moist lignocellulosic biomass feedstock into a dilute strong acid impregnator to effect pH values below about 3 for a sufficient residence time to render it acid-soaked and draining the acid-soaked biomass to about 30% to about 35% by weight solids;

b) dewatering said acid-soaked biomass by drying or centrifugation in a manner so as to prevent densifying the biomass particles and obtain a solids content of about 40% to 60% wet weight basis;

c) subjecting said acid-impregnated biomass to a first-stage hydrolysis reactor at a temperature sufficient to commence hydrolysis and discharging the formed hydrolysate into a first flash tank at a temperature sufficient to hydrolyze most of the soluble oligosaccharides to monomeric sugars and flashing remaining hydrolysate to a second flash tank at a lower temperature than the first flash tank—said second flash tank serving as a feed surge tank for a counter-current extractor;

d) washing the hydrolysate, recovering more than about 95% of the soluble sugars in the first-stage hydrolysate slurry by a counter-current extractor, and adjusting the pH of the extract to about 5;

e) subjecting remaining washed first stage pretreated solids to a second-stage acid and metal salt impregnator and dewatering by drying or centrifugation in a manner so as to prevent compaction of the biomass particles and obtain a solids content of about 40% to 60% wet weight basis;

f) subjecting said acid and metal salt-impregnated biomass to a second-stage hydrolysis reactor at a temperature of from about 190° C. to about 240° C. and discharging the formed hydrolysate into a flash tank at about 120° C. to about 140° C. to hydrolyze most of the remaining soluble oligosaccharides to monomeric sugars and flashing remaining hydrolysate to a second flash tank at a lower temperature than the first flash tank—said second flash tank serving as a feed surge tank for second-stage fermentors;

g) cooling the pH-adjusted extract from said counter-current extractor, feeding the extract to a first-stage fermentor and air sparging the first-stage fermentor at a rate sufficient to promote enough yeast growth to compensate for loss through second-stage fermentors;

h) pH adjusting second-stage hydrolysate slurry to about 4.5, cooling the slurry and adding it into the top of the first fermentor of the second-stage fermentation train, pumping broth from the bottom of the first fermentor to the top of a second fermentor for a period sufficient for the carried over yeast to consume over about 95% of fermentable sugars; and i) recovering ethanol.

2. The process of claim 1 wherein said reactor is a batch steam explosion reactor.

3. The process of claim 1 wherein said reactor is a continuous reactor.

4. The process of claim 1 wherein said lignocellulosic feedstock is selected from the group consisting of softwood, hardwood, agricultural residues, corn refining residues and grasses.

5. The process of claim 4 wherein said softwood is Douglas Fir, White Fir, Ponderosa Pine, Sitka spruce, and Hemlock.

6. The process of claim 4 wherein said municipal solid waste is construction lumber.

7. The process of claim 1 wherein said dilute(acid is selected from the group consisting of $H_2SO_4$, HCl, $HNO_3$, $SO_2$, and said metal salt catalyst is selected from the group consisting of ferrous sulfate, ferric sulfate, ferric chloride, aluminum sulfate, aluminum chloride, and magnesium sulfate.

8. The process of claim 7 wherein said acid is $H_2SO_4$ and said residence time is about 1 to about 60 minutes for first stage hydrolysis and about 1 to about 10 minutes for second stage hydrolysis.

9. The process of claim 8 wherein said temperature sufficient to commence hydrolysis is from about 130° C. to about 220° C. for first stage hydrolysis, and from about 190° C. to about 240° C. for second stage hydrolysis.

10. The process of claim 9 wherein said temperature sufficient to hydrolyze most of the soluble oligosaccharides to monomeric sugars in first flash tank is from about 120° C. to about 140° C., and the residence time of hydrolysate in the flash tank is from about 1 to about 3 hours.

11. The process of claim 7 wherein said acid is $SO_2$ and said residence time is about 1 to about 60 minutes.

12. The process of claim 11 wherein said temperature sufficient to commence hydrolysis is from about 130° C. to about 220° C. for first stage hydrolysis, and from about 190° C. to about 240° C. for second stage hydrolysis.

13. The process of claim 12 wherein said temperature sufficient to hydrolyze most of the soluble oligosaccharides to monomeric sugars in first flash tank is from about 120° C. to about 140° C., and the residence time of hydrolysate in the flash tank is from about 1 to about 3 hours.

14. The process of claim 7 wherein said acid is $H_2SO_4$, dewatering is by drying, and the acid concentration in the liquid in the biomass before subjecting to first stage or second stage hydrolysis is between about 0.3% to about 4.0% by weight, and the concentration of said metal salt is between about 0.2 to about 25.0 mmole/L.

15. The process of claim 7 wherein said acid is $SO_2$ and the feedstock is dewatered (if necessary) to 40% to 60% wet weight basis prior to $SO_2$ impregnation, and the acid concentration in the liquid in the biomass before subjecting to first stage or second stage hydrolysis is between about 0.3% to about 6.0% by weight.

16. The process of claim 1 wherein in step g) air sparging in the first fermentor of the first-stage fermentation train sufficient to promote yeast growth is about 0.05 wvm.

17. The process of claim 1 wherein in step g) air sparging sufficient to promote yeast growth is about 0.05 vvm.

18. The process of claim 1 wherein in step f) said lower temperature in said second flash tank is about 95° C.

19. The process in claim 1 wherein in step h) said whole slurry from the second stage hydrolysis reactor is fermented in the second train of fermentors using yeasts from the first stage fermentors.

20. The process of claim 1 wherein in step a) gaseous $SO_2$ is used as the acid, the solid content of biomass is between about 40% to about 60% by weight, and the dewatering step b) is omitted.

21. The process of claim 1 wherein said drying is done using heated air, nitrogen, carbon dioxide, superheated steam or any combination thereof.

22. The process of claim 1 wherein in step d) said extract is recovered hydrolysate liquor.

23. The process of claim 1 wherein in step e) said pretreated solids are insoluble solids.

* * * * *